United States Patent [19]

Liner et al.

[11] 4,038,149
[45] July 26, 1977

[54] LABORATORY TRAYS WITH LOCKABLE COVERS

[75] Inventors: John Liner, Woodbridge; Eric W. Soderberg, Milford, both of Conn.

[73] Assignee: Linbro Scientific, Inc., Hamden, Conn.

[21] Appl. No.: 645,550

[22] Filed: Dec. 31, 1975

[51] Int. Cl.² .................................................. C12B 1/00
[52] U.S. Cl. ...................................... 195/127; 23/259; 195/139
[58] Field of Search ................... 23/259; 195/127, 139

[56] References Cited

U.S. PATENT DOCUMENTS

| | | | |
|---|---|---|---|
| 3,107,204 | 10/1963 | Brown | 195/139 X |
| 3,297,184 | 1/1967 | Andelin | 195/139 |
| 3,537,956 | 11/1970 | Falcone | 195/139 |
| 3,597,326 | 8/1971 | Liner | 195/139 |
| 3,692,498 | 9/1972 | Frank | 23/259 |
| 3,729,382 | 4/1973 | Shaffer | 195/139 |
| 3,745,091 | 7/1973 | McCormick | 195/139 |
| 3,907,505 | 9/1975 | Beall | 23/259 |

Primary Examiner—Sidney Marantz
Attorney, Agent, or Firm—Walter Spruegel

[57] ABSTRACT

A laboratory tray with cup formations is on opposite sides of its upright circumferential wall provided with outwardly projecting pad formations with outer faces, with these pad formations registering with notches in a depending circumferential skirt on a cover in its closed position on the tray to clear the cover skirt and expose the outer pad faces in their entirety to an attendant's finger grasp for safe handling of the covered tray.

5 Claims, 5 Drawing Figures

LABORATORY TRAYS WITH LOCKABLE COVERS

This invention relates to laboratory trays with multicup formations and removable covers, and more particularly to laboratory trays with lockable covers.

Trays of the type with which the present invention is concerned are used for many laboratory procedures with test medium in some or all cup formations of the trays, with the cup formations being usually closed by top covers on the trays when the latter are in use, and most trays having on their top surfaces a few upright projections on which the closed covers rest to provide breathing clearance for media in the cup formations. To keep the closed covers in correct position over the cup formations on the trays and avoid their slide-off from the latter in any event, the covers have depending skirts which in closed cover position flank, and are also spaced by narrow breathing gaps from, the side and end walls of the trays. While such covered trays thus provide for subjection of different test media therein to the atmosphere, they have no ready provision to seal from the atmosphere other contained test media which require such sealing in many laboratory procedures. Therefore, in order at least to facilitate the sealing of contained test media in these trays from the atmosphere, the trays and covers are fashioned to accomplish such sealing by resorting to simple adhesive tape and fairly easy as well as readily sealing application of such tape to covered trays. To this end, the depending skirt on each cover is of a height at which a preferred outward bottom flange formation thereon is, in closed cover position on a tray, vertically spaced from a similar bottom flange formation on the tray by a rather narrow circumferential gap, and a length of adhesive tape is evenly stuck to the superposed flange formations by simply finger-wrapping the tape therearound in the course of which the tape will readily bridge the gap therebetween due to its narrow width and, hence, will reliably seal this gap from the atmosphere. However, while the depending skirts on the covers for the trays are, by virtue of their considerable height, advantageous in that they contribute toward fairly ready and reliable sealing of contained test media in the trays when required, they are anything but conducive to ready handling of covered trays because the applied covers keep all but the bottoms of the trays out of the grasp of attendants. The handling by attendants of covered trays is, therefore, an awkward and even precarious task, and it happens all too frequently that in handling a covered tray a laboratory test procedure may be ruined either by breakage of an applied seal or by spillage from a tray of contained test medium which, moreover, may be of a kind that is hazardous to an attendant if coming into contact therewith.

It is among the objects of the present invention to provide coverable trays of this type with finger grip surfaces which, with or without applied covers on the trays, are readily perceptible as well as highly suggestive of their designated finger grip function and afford to attendants convenient and secure finger holds on the trays, with these finger grip surfaces being arranged to permit retention, to all practical intents and purposes, of those elements of prior trays and covers which proved to serve so well in sealing contained test medium in covered trays from the atmosphere and, in consequence, became widely adopted as distinct characteristics of such trays and covers, namely, depending circumferential skirts with bottom flange formations on the covers and fairly close spacing of these flange formations from similar bottom flange formations on the trays in closed cover position.

It is another object of the present invention to provide trays and covers of this type, of which the aforementioned finger grip surfaces on the trays are provided by the outer faces of simple pad formations on opposite sidewalls of the trays, with the depending skirts on the covers having notches in which the pad formations on the trays extend for clearance from the covers when the latter are closed on the trays, and the opposite pad faces on a tray being of adequate areas for convenient and secure grip between the thumb and a finger of an attendant's hand. With this arrangement, a covered tray can be handled, including lifted from a support, easily and securely with one hand, and can securely be grasped with one's hand even by feel of touch alone if need be. Further, by keeping the pad formations on the opposite sidewalls of the trays at an outward projection therefrom at which the finger grip faces thereof are flush, more or less, with the adjacent skirts on closed covers thereon, a closed cover on a tray may even be held locked to the latter when an attendant's finger grip is easily and even instinctively extended from the outer pad faces on the tray to adjacent portions of the skirt on the closed cover. Also, with the pad formations on the trays and the clearance notches therefor in the skirts on the covers requiring certain orientation between them for their proper functioning in the closed trays, their orientation may be such that the covers may close on the trays in only one position thereon as is preferred in some laboratory test procedures.

Further objects and advantages will appear to those skilled in the art from the following, considered in conjunction with the accompanying drawings.

In the accompanying drawings.

Figures 1, 2:
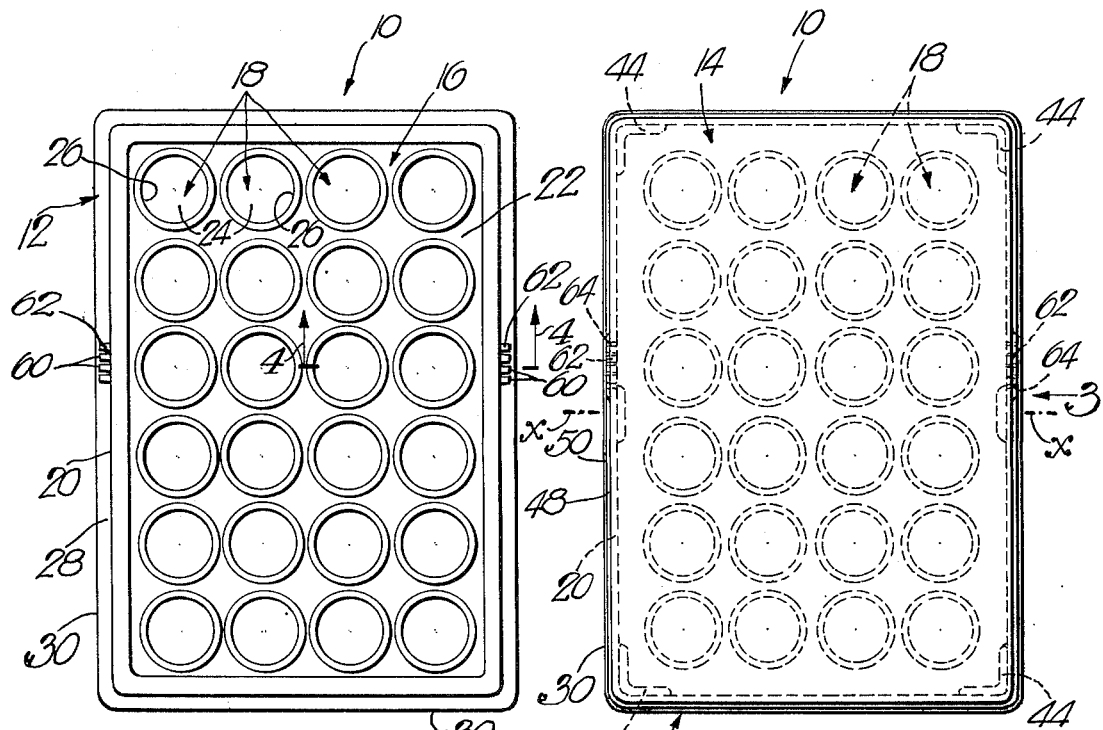
FIG. 1 is a top view of a tray embodying the invention.
FIG. 2 is a top view of the same tray with a closed cover thereon.

Referring to the drawings, the reference numeral 10 designates a laboratory unit which provides a tray 12 and a cover 14 therefor. The tray 12, which is preferably molded of any suitable transparent plastic, has a top 16, a plurality of identical cup formations 18 which are open at the top 16, and a circumferential wall 20 depending from the top 16. The tray top 16 is formed by a wall 22, and each cup formation 18 has a bottom wall 24 and an annular rim or sidewall 26 which is continuous with the top wall 22. The cup formations 18, which may be of any given conventional size, may be used for many different purposes, such as for plaguing, immunodiffusion, virus isolation, hemadsorption, viral inhibition, clinical bacteriology and cell growth, for example. The tray 12 is in this instance rectangular, and the cup formations are arranged in parallel longitudinal and transverse rows. The circumferential tray wall 20 has an outward bottom flange 28 with an outer surface 30.

The cover 14, which is also preferably molded of any suitable transparent plastic, has a plane top wall 38 and a depending circumferential skirt 40, with the inner surface 42 of the top wall 38 of the cover 14 having in this instance shallow ridges 44 which in closed cover position rest on the tray top 16 to keep the cover surface 42 spaced from the tray top 16 by a relatively narrow gap $g$. The cover skirt 40 is in closed cover position in overlap relation with the circumferential tray wall 20 and is also spaced therefrom throughout by a relatively narrow gap $g'$. The gap $g,g'$ between the tray 12 and closed cover 14 thereon is intended for a "breathing" purpose, i.e., subjection of medium in cup formations 18 to the atmosphere or free diffusion of the gaseous environment inside and outside the tray.

Figure 3:
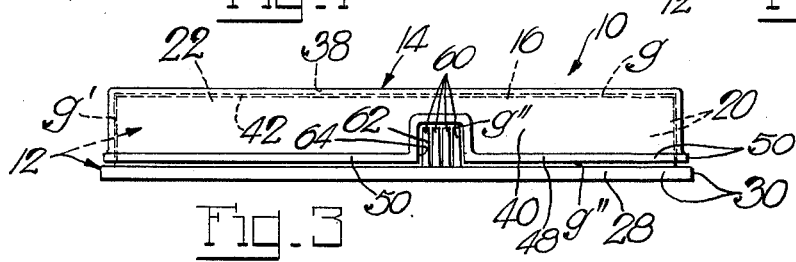
FIG. 3 is a side view of the covered tray as seen in the direction of the arrow 3 in FIG. 2.
Figures 4, 5:
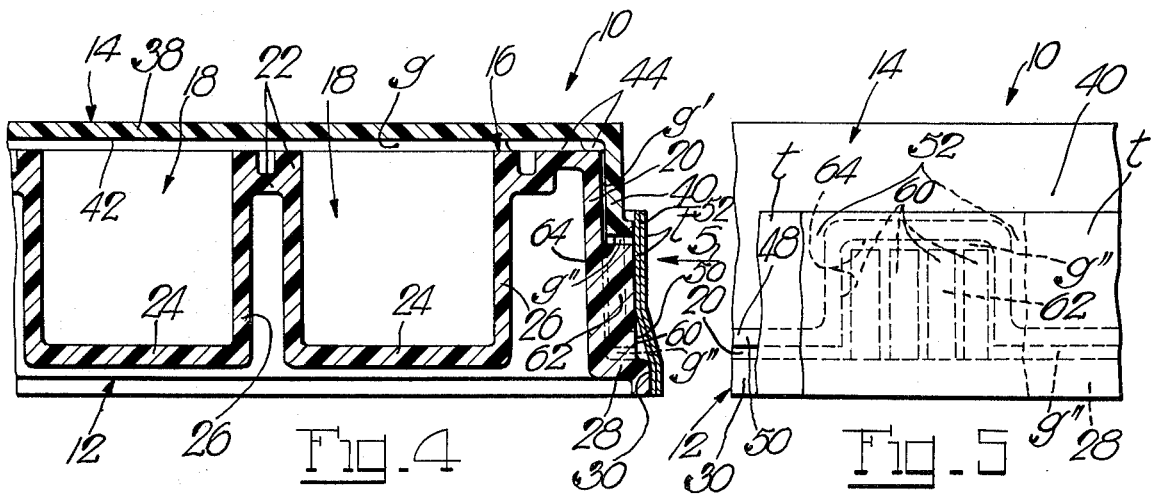
FIG. 4 is an enlarged fragmentary section through the tray taken substantially on the line 4—4 of FIG. 1, with the cover in closed position thereon.
FIG. 5 is an enlarged fragmentary side view of the covered tray as seen in the direction of the arrow 5 in FIG. 4.

The cover further has at the bottom of its depending skirt 40 an outward flange 48 with an outer surface 50 which in closed cover position is flush, more or less, with the outer surface 30 of the bottom flange 28 on the tray 12 (FIGS. 3 and 4), and the bottom flange 48 on the cover is in closed cover position spaced from the bottom flange 28 on the tray by another narrow gap $g''$ which is continuous with the gap $g,g'$ between the tray and closed cover. The outer surfaces 30 and 50 of the bottom flanges 28 and 48 on the tray and cover are thus available as conveniently accessible application surfaces for a strip of adhesive tape $t$ which is readily finger-wrapped around these surfaces 30 and 50 and overlapped at its ends as at 52 (FIGS. 4 and 5) to bridge the narrow circumferential gap $g''$ between tray and cover and thereby reliably seal the interior of the tray from the atmosphere as is required in certain tests.

While the narrow gap $g''$ between the tray and closed cover is thus advantageous for reliable sealing of the closed tray if required, it also leaves the depending skirt 40 on the cover sufficiently high to leave very little of the sides of the covered tray accessible to an attendant's grasp for manipulation, including lifting, of the tray as is frequently necessary when the tray is in use. Handling of the covered tray, especially with only one hand as is mostly done, is, therefore, an awkward and even precarious task, and it happens all too frequently that in handling a covered tray either clumsily or by even dropping it, a test procedure is ruined either by breakage of an applied seal or by spillage from the tray of contained medium which, moreover, may be of a kind that is hazardous to an attendant if coming into contact therewith. In order to avoid such mishap and greatly facilitate handling of the covered tray, the tray 12 is on opposite sides of its circumferential wall 20 provided with finger grip surfaces 60 which with or without the cover on the tray are accessible to an attendant's finger grasp for handling, including lifting, the tray in an entirely convenient manner. To this end, the finger grip surfaces 60 are provided by the outer faces of opposite pad formations 62 on the circumferential tray wall 20, with these outer pad faces 60 being of sufficient area extent for secure and convenient grip by an attendant's fingers. In order to keep these outer pad faces 60 fully accessible to an attendant's finger grip, preferably and conveniently between two spread digits, i.e., thumb and a finger, of one of the attendant's hands, the depending skirt 40 of the cover 14 is on opposite sides thereof provided with notches 64 which in closed cover position on the tray clear the pad formations 62 and thus leave the outer pad faces 60 fully exposed to the attendant's fingers. The outer pad faces 60 are preferably ridged to enhance an attendant's finger grip thereon. Of course, the pad formations 62 on the tray 12 and the clearance notches 64 therefor in the cover skirt 40 are properly coordinated for their registry in properly closed cover position on the tray. In this instance, the pad formations 62 and clearance notches 64 are offset from the median axis $x$ of the covered tray (FIG. 2) so that they will register in only one closed position of the cover on the tray. In closed position of the cover on the tray, the outer pad faces 60 on the tray are preferably substantially flush with the adjacent notched portions of the cover skirt 40 so that in holding the covered tray at the pad faces 60, an attendant's fingers on the latter lap over the adjacent notched cover skirt portions and thereby also lock the closed cover to the tray.

What is claimed is:

1. A laboratory unit, comprising a tray with a top surface, a bottom, an upright circumferential wall extending from said top surface to said bottom, and a plurality of cup formations extending downwardly from, and being open at, said top surface; and a removable cover having a top wall and a therefrom depending circumferential skirt overlapping said circumferential tray wall in closed cover position in which said top walls rests on said top surface of said tray, with said tray also having pad formations with outer faces on said circumferential wall on opposite sides thereof and extending substantially from said tray bottom heightwise to a level within the confines of said cover skirt in closed cover position, and said cover skirt having notches with which said pad formations register in closed cover position for clearance from said cover skirt and reach of said pad faces in their entirety by an attendant's fingers for secure grasp by the latter of the covered tray.

2. A laboratory unit as in claim 1, in which each of said outer pad faces is of an area for secure gripping engagement by an attendant's finger, and said outer faces of said pad formations on said opposite sides of said circumferential tray wall are spaced for reach by outstretched thumb and finger digits of an attendant's hand.

3. A laboratory unit as in claim 2, in which said cover skirt has an outer surface substantially flush with said outer pad faces in said closed cover position.

4. A laboratory unit as in claim 2, in which said outer pad faces are ridged for enhanced finger grip by an attendant.

5. A laboratory unit as in claim 2, in which said pad formations on said circumferential tray wall and said notches in said cover skirt are coordinated for their registry in only one closed cover position on the tray.

* * * * *